US010026057B1

(12) United States Patent
Elsherif

(10) Patent No.: US 10,026,057 B1
(45) Date of Patent: Jul. 17, 2018

(54) RETAIL CIGARETTE INVENTORY-MONITORING SYSTEM

(71) Applicant: Hussein Elsherif, East Lyme, CT (US)

(72) Inventor: Hussein Elsherif, East Lyme, CT (US)

( * ) Notice: Subject to any disclaimer, the term of this patent is extended or adjusted under 35 U.S.C. 154(b) by 0 days.

(21) Appl. No.: 15/590,207

(22) Filed: May 9, 2017

(51) Int. Cl.
A47F 10/00 (2006.01)
G06Q 10/08 (2012.01)
G06M 9/00 (2006.01)
A61M 15/06 (2006.01)

(52) U.S. Cl.
CPC .......... *G06Q 10/087* (2013.01); *A61M 15/06* (2013.01); *G06M 9/00* (2013.01)

(58) Field of Classification Search
CPC ...... G06Q 10/087; A61M 15/06; G06M 9/00; A47F 10/00
USPC ................. 340/568.1, 5.92; 211/59.3, 6, 134
See application file for complete search history.

(56) References Cited

U.S. PATENT DOCUMENTS

| 5,881,910 | A  | * | 3/1999  | Rein ..................... A47F 1/126 221/6 |
| 7,224,762 | B2 |   | 5/2007  | Koger |
| D553,384  | S  |   | 10/2007 | Wilenius |
| 7,813,973 | B2 |   | 10/2010 | Gudbjartsson |
| 8,260,456 | B2 |   | 9/2012  | Siegel |
| 8,938,396 | B2 | * | 1/2015  | Swafford, Jr. .......... A47F 1/126 705/22 |
| 9,730,531 | B2 | * | 8/2017  | Hardy ..................... A47F 1/126 |
| 2005/0040123 | A1 | * | 2/2005 | Ali ........................ A47F 1/126 211/59.3 |
| 2005/0279722 | A1 | * | 12/2005 | Ali ........................ A47F 10/00 211/59.3 |
| 2009/0135013 | A1 | * | 5/2009 | Kushida ................. G06Q 10/08 340/568.1 |
| 2009/0319399 | A1 | * | 12/2009 | Resta ..................... G06Q 10/00 705/28 |
| 2010/0258513 | A1 | * | 10/2010 | Meyer .................... A47F 1/126 211/59.3 |
| 2012/0091162 | A1 | * | 4/2012 | Overhultz .............. A47F 1/126 221/1 |
| 2012/0215726 | A1 | * | 8/2012 | Ip ............................ G07G 1/06 705/500 |
| 2016/0134930 | A1 | * | 5/2016 | Swafford ............. A47F 5/0068 725/80 |
| 2016/0321603 | A1 | * | 11/2016 | Williams ............ G06Q 10/087 |

FOREIGN PATENT DOCUMENTS

WO    2016077597    5/2016

* cited by examiner

*Primary Examiner* — Firmin Backer
*Assistant Examiner* — Munear Akki

(57) ABSTRACT

The retail cigarette inventory-monitoring system is configured for use with a plurality of prepackaged smoking materials. Each of the plurality of prepackaged smoking materials is a container referred to as a pack. The retail cigarette inventory-monitoring system is a storage system configured for use in storing the plurality of prepackaged smoking materials. The retail cigarette inventory-monitoring system comprises a package rack and a counting device. The counting device attaches to the package rack. The package rack stores as individual packs each pack contained within the plurality of prepackaged smoking materials. The counting device automatically counts the number of packs contained within the plurality of prepackaged smoking materials contained within the package rack of the retail cigarette inventory-monitoring system.

1 Claim, 4 Drawing Sheets

RETAIL CIGARETTE INVENTORY-MONITORING SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of instruments and counting, more specifically, a device for counting objects in a stack.

SUMMARY OF INVENTION

The retail cigarette inventory-monitoring system is configured for use with a plurality of prepackaged smoking materials. Each of the plurality of prepackaged smoking materials is a container formed in a shape selected from the group consisting of a rectangular block or a disk. Each of the plurality of prepackaged smoking materials is a container referred to as a pack. It is anticipated that the pack will contain a premeasured quantity of a smoking material. The pack format is selected from the group consisting of a rigid pack or a soft sided pack. The rigid pack is often referred to as a "hard" or "hard sided" pack. The retail cigarette inventory-monitoring system is a storage system configured for use in storing the plurality of prepackaged smoking materials. The retail cigarette inventory-monitoring system comprises a package rack and a counting device. The counting device attaches to the package rack. The packaging rack stores as individual packs each pack contained within the plurality of prepackaged smoking materials. The counting device automatically counts the number of packs contained within the plurality of prepackaged smoking materials contained within the retail cigarette inventory-monitoring system.

These together with additional objects, features and advantages of the retail cigarette inventory-monitoring system will be readily apparent to those of ordinary skill in the art upon reading the following detailed description of the presently preferred, but nonetheless illustrative, embodiments when taken in conjunction with the accompanying drawings.

In this respect, before explaining the current embodiments of the retail cigarette inventory-monitoring system in detail, it is to be understood that the retail cigarette inventory-monitoring system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the retail cigarette inventory-monitoring system.

It is therefore important that the claims be regarded as including such equivalent construction insofar as they do not depart from the spirit and scope of the retail cigarette inventory-monitoring system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
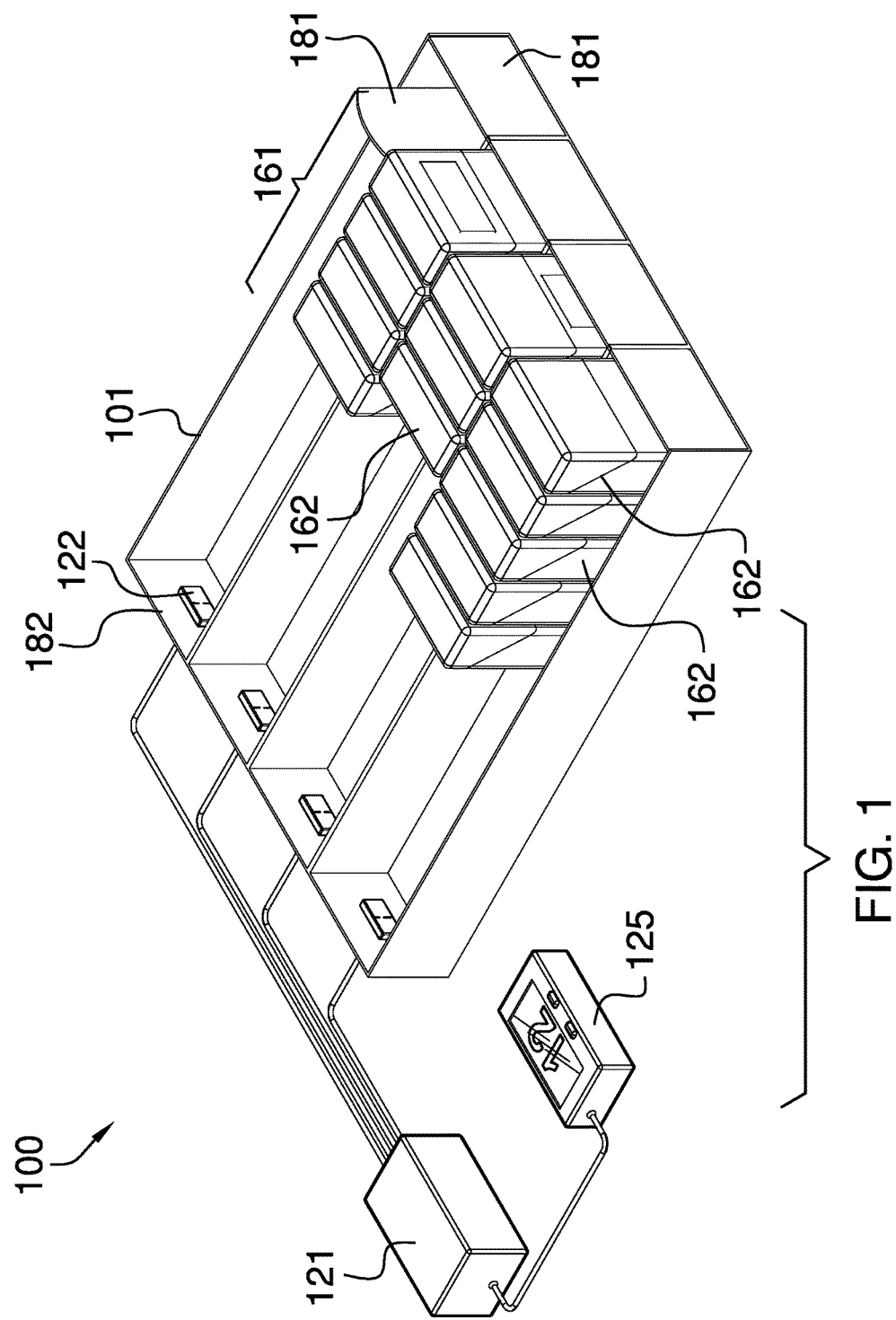
FIG. 1 is a perspective view of an embodiment of the disclosure.
Figure 2:
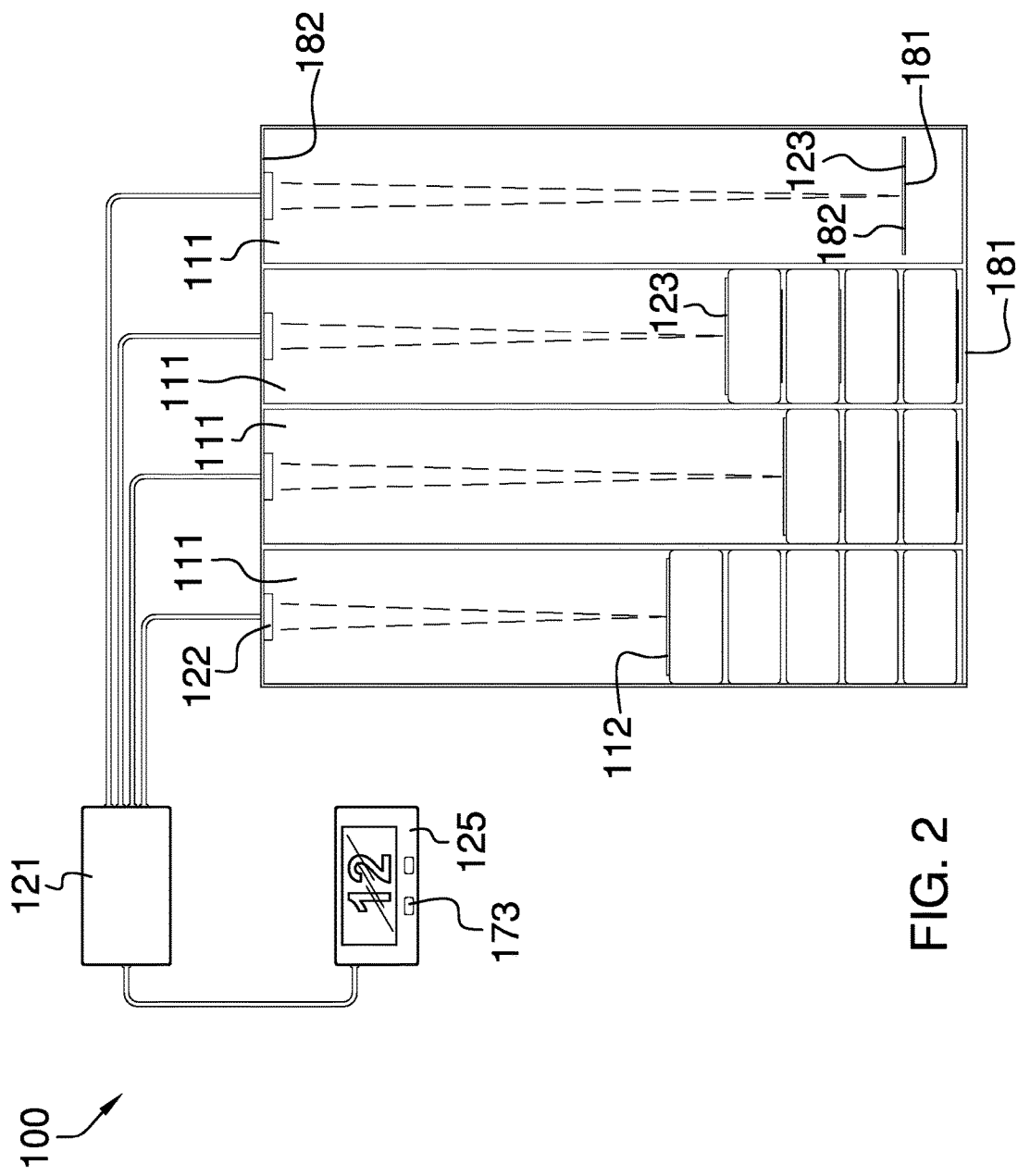
FIG. 2 is a top view of an embodiment of the disclosure.
Figure 3:
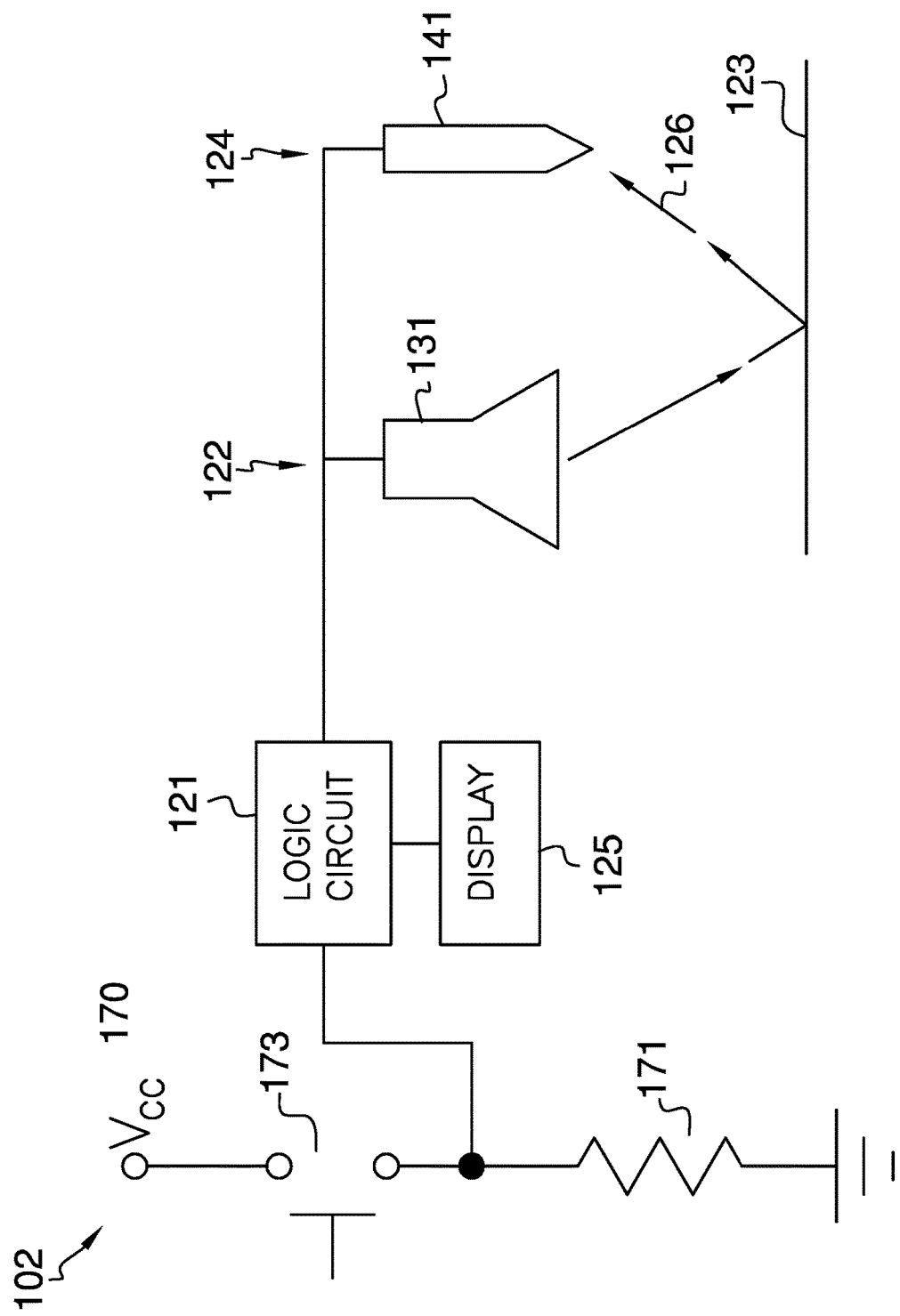
FIG. 3 is a schematic of an embodiment of the disclosure.
Figure 4:
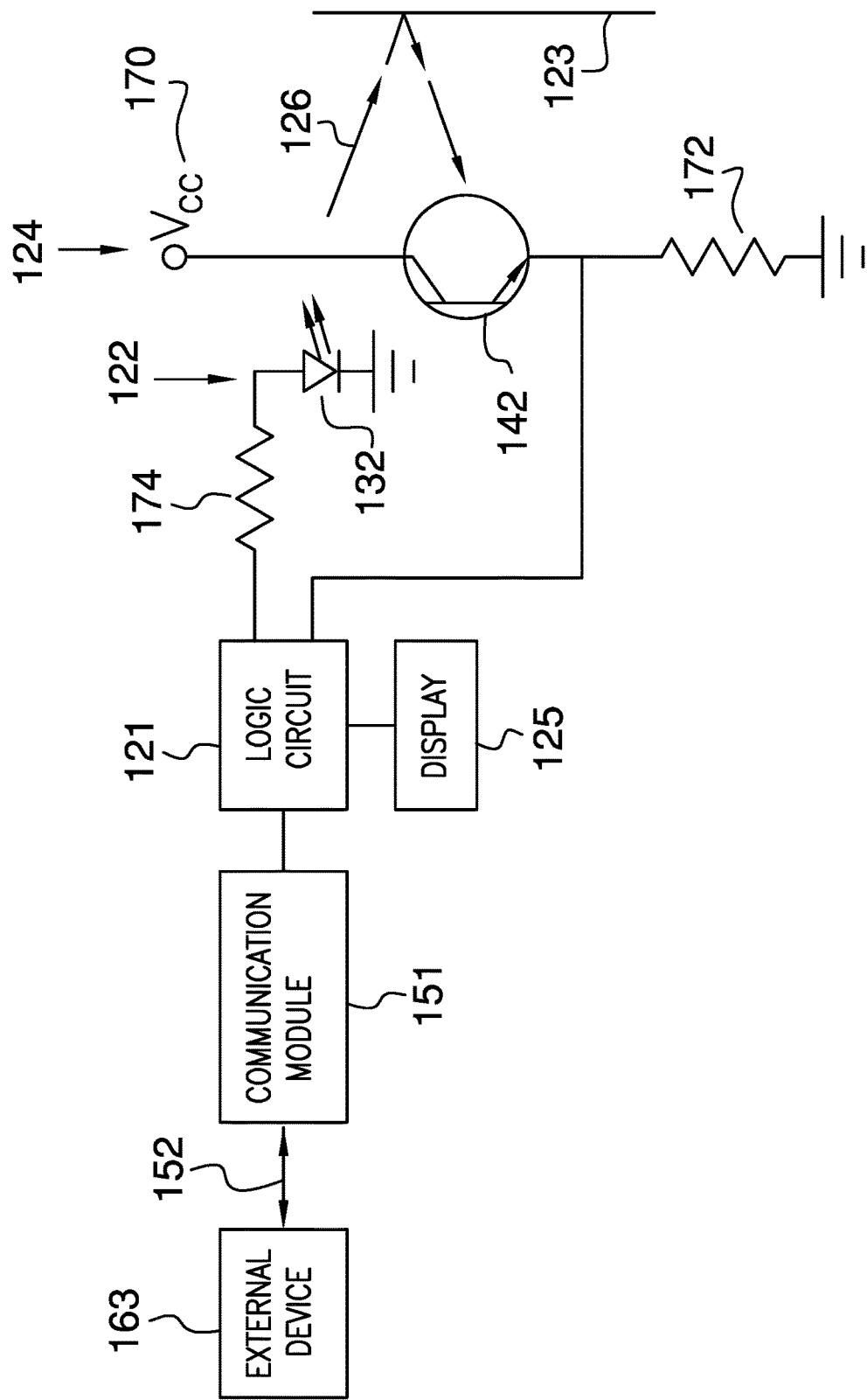
FIG. 4 is a schematic of an alternate embodiment of the disclosure.

Detailed reference will now be made to one or more potential embodiments of the disclosure, which are illustrated in FIGS. 1 through 4.

The retail cigarette inventory-monitoring system 100 (hereinafter invention) is configured for use with a plurality of prepackaged smoking materials 161. Each of the plurality of prepackaged smoking materials 161 is a container formed in a shape selected from the group consisting of a rectangular block or a disk. Each of the plurality of prepackaged smoking materials 161 is a container referred to as a pack 162. It is anticipated that the pack 162 will contain a premeasured quantity of a smoking material. The pack 162 format is selected from the group consisting of a rigid pack 162 or a soft sided pack 162. The rigid pack 162 is often referred to as a "hard" or "hard sided" pack 162. The invention 100 is a storage system configured for use in storing the plurality of prepackaged smoking materials 161. The invention 100 comprises a package rack 101 and a counting device 102. The counting device 102 attaches to the package rack 101. The package rack 101 stores as an individual pack 162 each pack 162 contained within the plurality of prepackaged smoking materials 161. The counting device 102 automatically counts the number of packs 162 contained within the plurality of prepackaged smoking materials 161 contained within the package rack 101 of the invention 100.

The package rack 101 is a commercially available tobacco rack that is commonly used to organize and dispense individual packs 162 of smoking materials. The package rack 101 can be seen at most locations that sell individual packs 162 of a tobacco based smoking material. The package rack 101 is modified to accommodate the counting device 102 as described in this disclosure. The package rack 101 comprises a plurality of carton trays 111.

Each individual carton tray selected from the plurality of carton trays 111 comprises a pushing device 112 and a track 113. The plurality of carton trays 111 is further defined with a front side 181 and a rear side 182. The pushing device 112 is further defined with a front side 181 and a rear side 182. The front side 181 of the pushing device 112 faces the front side 181 of the plurality of carton trays 111. The rear side 182 of the pushing device 112 faces the rear side 182 of the plurality of carton trays 111. The front side 181 refers to the side of the package rack 101 into which and from which each of the plurality of prepackaged smoking materials 161 are installed and removed. The rear side 182 refers to the side of the package rack 101 that is distal from the front side 181.

The plurality of prepackaged smoking materials 161 is stored within the plurality of carton trays 111. The plurality of carton trays 111 is segmented such that the plurality of prepackaged smoking materials 161 can be organized by brand and type of pack 162.

The track 113 is a hollow rectangular block structure within which the plurality of prepackaged smoking materials 161 are placed for storage and distribution. A manufacturer of the package rack 101 will commonly refer to the track 113 as a column. The pushing device 112 is installed within the track 113. The pushing device 112 is a spring loaded plate shaped device that pushes the individual packs 162 of smoking material to the front side 181 of the plurality of carton trays 111. Each pushing device 112 within the package rack 101 pushes the plurality of prepackaged smoking materials 161 towards the front of the package rack 101.

The counting device 102 is an automated system that counts: 1) the total number of individual packs of smoking material contained within the plurality of prepackaged smoking materials 161; and, 2) the total number of individual pack 162 of smoking material contained with each individual track 113 selected from the plurality of carton trays 111 of the package rack 101. The counting device 102 comprises a logic module 121, a wavefront 126 generator 122, a wavefront 126 sensor 124, and a display 125. The logic module 121 is further defined with a timing circuit. The counting device 102 further comprises a reflecting surface 123 that is attached to the pushing device 112 of the track 113 selected from the plurality of carton trays 111.

The logic module 121 is a readily and commercially available electronic device that is used to manage, regulate, and operate the counting device 102. Depending on the design, the logic module 121 may be an electronic circuit or a programmable electronic device.

The wavefront 126 generator 122 is an electrical device that generates the wavefront 126. The wavefront 126 generator 122 is mounted on the rear side 182 of each track 113 such that the generated wavefront 126 moves towards the pushing device 112.

The reflecting surface 123 is a smooth and reflective surface that is mounted on the rear side 182 of the pushing device 112. The reflecting surface 123 reflects the wavefront 126 generated by the wavefront 126 generator 122 to the wavefront 126 sensor 124.

The wavefront 126 sensor 124 is an electrical sensor that detects the wavefront 126 after it has been reflected off the reflecting surface 123. The wavefront 126 sensor 124 is mounted on the rear side 182 of each track 113 such that the reflected wavefront 126 is detected by the wavefront 126 sensor 124.

The display 125 is an electrical device that is used to display pack 162 count data as accumulated by the counting device 102. Methods to select and use a commercially available display 125 are well known and documented in the electrical arts.

The wavefront 126 is a wave based source of energy that travels at a known constant speed. Within this disclosure, the energy source may be light based or acoustically based.

In the first potential embodiment of the disclosure, the wavefront 126 generator 122 comprises a speaker 131 and the wavefront 126 sensor 124 comprises a microphone 141. In the first potential embodiment of the disclosure, the counting device 102 further comprises a trigger 173, a first pull down resistor 171, and an externally provided voltage referred to as the VCC 170. The VCC 170 refers to a voltage that is described in more detail elsewhere in this disclosure.

The speaker 131 is an electrical device is used to generate an audible wavefront 126. The microphone 141 is a readily and commercially available transducer that converts audible energy into an electrical signal. The first pull down resistor 171 is an electrical resistor that is used to present the VCC 170 to the logic module 121 to indicate that the trigger 173 has been actuated. The trigger 173 is a momentary switch that is used to initiate the counting device 102.

The trigger 173 is wired in series between the VCC 170 and the first pull down resistor 171. The first pull down resistor 171 is wired in series between the trigger 173 and the electrical ground. The logic module 121 detects the VCC 170 across the first pull down resistor 171 between the trigger 173 and the first pull down resistor 171.

In a second potential embodiment of the disclosure, the wavefront 126 generator 122 comprises a LED 132 and the wavefront 126 sensor 124 comprises a photoswitch 142. In the second potential embodiment of the disclosure, the counting device 102 further comprises a communication module 151, a second pull down resistor 172, a limit resistor 174, and the VCC 170. The VCC 170 refers to a voltage that is described in more detail elsewhere in this disclosure. In the second potential embodiment of the disclosure, the logic module 121 is programmable The LED 132 is an electrical device is used to generate a visible wavefront 126. The photoswitch 142 is a readily and commercially available switch that is actuated by light. The photoswitch 142 is designed to close in the presence of light and to open in the absence of light. The second pull down resistor 172 is an electrical resistor that is used to present the VCC 170 to the logic module 121 to indicate that the photoswitch 142 has detected the wavefront 126. The limit resistor 174 is an electrical resistor that is used to limit current flow through the LED 132.

The communication module 151 is a readily and commercially available wireless electronic communication device that allows the logic module 121 to communicate with an externally provided electronic device 163 such as a personal data device or a computer network. The communication module 151 creates a wireless link 152 with the externally provided electronic device 163 for this purpose. The protocol selected for the wireless link 152 created by the communication module 151 is selected from the group consisting of Bluetooth, WiFi, or the use of a commercially provided and publicly available cellular wireless network In the second potential embodiment of the disclosure, the communication module 151 communicates SMS and MMS messages between the logic module 121 and the externally provided electronic device 163 of an appropriate authority through a commercially provided and publicly available cellular wireless network. The use of a commercially provided and publicly available cellular wireless network is preferred because: 1) of its low cost; 2) of its widespread availability and broad interoperability between competing commercially provided and publicly available cellular wireless networks; and, 3) methods and techniques to send SMS and MMS messages over a commercially provided and publicly available cellular wireless network are well known and documented by those skilled in the electrical arts.

The photoswitch 142 is wired in series between the VCC 170 and the second pull down resistor 172. The second pull down resistor 172 is wired in series between the photoswitch 142 and the electrical ground. The logic module 121 detects the VCC 170 across the second pull down resistor 172 between the photoswitch 142 and the second pull down resistor 172.

The operation of the counting device 102 is described in the following 3 paragraphs.

Within this disclosure, it is assumed that each pack 162 contained within a track 113 selected from the plurality of carton trays 111 will have identical and known dimensions. It is further assumed that the distance from the front side 181 to the rear side 182 of the selected track 113 is known.

To count the packs 162 within a selected track 113, the logic module 121 simultaneously initiates a wavefront 126 from the wavefront 126 generator 122 while starting a timing device based on a timing circuit contained with the logic module 121. The reflecting surface 123 is mounted on the rear side 182 of the pushing device 112 such that the generated wavefront 126 will be reflected to the wavefront 126 sensor 124. Upon detection of the wavefront 126, the logic module 121 ends the operation of the timing device and calculates the distance from the wavefront 126 generator 122 to the wavefront 126 sensor 124 using the measured time and the known speed of the wavefront 126. One half of the distance from the wavefront 126 generator 122 to the wavefront 126 sensor 124 is a measure of the "empty" space within the selected track 113.

By incorporating the known overall length of the selected track 113 and the known dimensions of an individual pack 162 it becomes possible for the logic module 121 to calculate the number of packs 162 within a selected track 113. The logic module 121 performs this calculation for each column within the plurality of carton trays 111 and then uses the display 125 as an interface to communicate: 1) the total number of packs 162 in the plurality of carton trays 111; and, 2) the number of individual packs 162 within each selected column of the plurality of carton trays 111 to an appropriate authority. In the second potential embodiment of the disclosure, the logic module 121 further transmits this information over the wireless link 152 to the externally provided electronic device 163 using the communication module 151.

The following definitions were used in this disclosure:

Appropriate Authority: As used in this disclosure, an appropriate authority is a previously determined person or organization that is designated to receive alarm or other notification messages regarding a monitored system or activity.

Bluetooth: As used in this disclosure, Bluetooth is a standardized communication protocol that is used to wirelessly interconnect electronic devices.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends.

Diode: As used in this disclosure, a diode is a two terminal semiconductor device that allows current flow in only one direction. The two terminals are called the anode and the cathode. Electric current is allowed to pass from the anode to the cathode.

Disk: As used in this disclosure, a disk is a cylindrically shaped object that is flat in appearance.

Display: As used in this disclosure, a display is a surface upon which is presented an image, potentially including, but not limited to, graphic images and text, that is interpretable by an individual viewing the projected image in a meaningful manner.

Electrical Ground: As used in this disclosure, an electrical ground is a common reference voltage that is used in the design and implementation of electrical circuits. An electrical ground is often, but not necessarily, the discharge point of electric currents flowing through an electric circuit.

IEEE: As used in this disclosure, the IEEE (pronounced "I triple E") is an acronym for the Institute for Electrical and Electronic Engineers.

Interface: As used in this disclosure, an interface is a physical or virtual boundary that separates two different systems across which information is exchanged.

LED: As used in this disclosure, an LED is an acronym for a light emitting diode. A light emitting diode is a diode that is also a light source.

Logic Module: As used in this disclosure, a logic module is a readily and commercially available electrical device that is programmable and that accepts digital and analog inputs, processes the digital and analog inputs according to previously stored instruction and provides the results of these instructions as digital or analog outputs.

Microphone: As used in this disclosure, a microphone is a transducer that converts the energy from vibration into electrical energy. The sources of vibrations include, but are not limited to, acoustic energy.

Momentary Switch: As used in this disclosure, a momentary switch is a biased switch in the sense that the momentary switch has a baseline position that only changes when the momentary switch is actuated (for example when a pushbutton switch is pushed). The momentary switch then returns to the baseline position once the actuation is completed. This baseline position is called the "normal" position. So for example, a "normally open" momentary switch interrupts (open) the electric circuit in the baseline position and completes (closes) the circuit when the momentary switch is activated. Similarly, a "normally closed" momentary switch will complete (close) an electric circuit in the baseline position and interrupt (open) the circuit when the momentary switch is activated.

Personal Data Device: As used in this disclosure, a personal data device is a handheld device that is used for managing personal information and communication. Examples of personal data device include, but are not limited to, cellular phones, tablets and smart phones.

Photoelectric: As used in this disclosure, photoelectric is an adjective used to describe an electronic component in which the performance of the electronic component is modified by light. Typical photoelectric devices include, but are not limited to, photoelectric transistors, photoelectric diodes, and photoelectric resistors.

Photoswitch: As used in this disclosure, a photoswitch is a switch that is actuated with light. The operation of a photoswitch is often based on the use of a photoelectric device.

Plate: As used in this disclosure, a plate is a smooth, flat and semi-rigid or rigid structure that has at least one dimension that: 1) is of uniform thickness; and 2) that appears thin relative to the other dimensions of the object. Plates often have a rectangular or disk like appearance.

Rectangular Block: As used in this disclosure, a rectangular block refers to a three dimensional structure comprising six rectangular surfaces formed at right angles. Within this disclosure, a rectangular block may further comprises rounded edges and corners.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Smoking Material: As used in this disclosure, smoking materials are combustible materials that are intended to be deeply inhaled while they are being burned. This definition is intended to include, but is not limited to, tobacco and materials that exhibit pharmacological activity such as marijuana. This definition is intended to exclude combustible materials that are burned as a perfume but that are generally not purposefully inhaled including, but not limited to, incense and scented oils.

SMS: As used in this disclosure, SMS is an abbreviation for short message service. The short message service is a service that is often provided with the cellular services that support personal data devices. Specifically, the SMS allows for the exchange of written messages between personal data devices. The SMS is commonly referred to as text messaging. A common enhancement of SMS is the inclusion of the delivery of multimedia services. This enhanced service is often referred to as Multimedia Media Services which is abbreviated as MMS.

Speaker: As used in this disclosure, a speaker is an electrical device that converts an electrical signal into an audible sound.

Spring: As used in this disclosure, a spring is a device that is used to store mechanical energy. This mechanical energy will often be stored by: 1) deforming an elastomeric material that is used to make the device; 2) the application of a torque to a rigid structure; or 3) a combination of the previous two items.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Timing Circuit: As used in this disclosure, a timing circuit refers to an electrical network of interconnected electrical elements, potentially including but not limited to, resistors, capacitors, diodes, transistors, and integrated circuit devices. The purpose of the timing circuit is to generate an electrical control signal after a predetermined amount of time. In common usage, a timing circuit is also referred to as timing circuitry.

Timing Device: As used in this disclosure, a timing device is an automatic mechanism for activating or deactivating a device at a specific time.

Transducer: As used in this disclosure, a transducer is a device that converts a physical quantity, such as pressure or brightness into an electrical signal or a device that converts an electrical signal into a physical quantity.

Vcc: As used in this disclosure, Vcc is an acronym for Voltage at the Common Collector. Technically, the Vcc is the primary power source for an NPN transistor. In this disclosure, the definition of Vcc is more broadly defined to mean a direct current voltage source.

WiFi: As used in this disclosure, WiFi refers to the physical implementation of a collection of wireless electronic communication standards commonly referred to as IEEE 802.11x.

Wireless: As used in this disclosure, wireless is an adjective that is used to describe a communication channel between two terminals that does not require the use of physical cabling.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:
1. A device for counting objects in a stack comprising:
a package rack and a counting device;
wherein the counting device attaches to the package rack;
wherein the device for counting objects is configured for use with a plurality of prepackaged smoking materials;
wherein each of the plurality of prepackaged smoking materials is a container formed in a shape selected from the group consisting of a rectangular block or a disk;
wherein each of the plurality of prepackaged smoking materials is a container referred to as a pack;
wherein the pack contains a premeasured quantity of a smoking material;
wherein the device for counting objects is a storage system configured for use in storing the plurality of prepackaged smoking materials;
wherein the package rack stores as an individual pack each pack contained within the plurality of prepackaged smoking materials;

wherein the counting device automatically counts the number of packs contained within the plurality of prepackaged smoking materials contained within the package rack of the device for counting objects;

wherein the package rack comprises a plurality of carton trays;

wherein each individual carton tray selected from the plurality of carton trays comprises a pushing device and a track;

wherein the pushing rack is installed in the track;

wherein the plurality of carton trays is further defined with a front side and a rear side;

wherein the pushing device is further defined with a front side and a rear side;

wherein the front side of the pushing device faces the front side of the plurality of carton trays;

wherein the rear side of the pushing device faces the rear side of the plurality of carton trays;

wherein the rear side refers to the side of the package rack that is distal from the front side;

wherein the plurality of prepackaged smoking materials is stored within the plurality of carton trays;

wherein the track is a hollow rectangular block structure;

wherein the pushing device is installed within the track of each of the plurality of carton trays;

wherein the pushing device is a spring loaded plate shaped device;

wherein each pushing device within the package rack pushes the plurality of prepackaged smoking materials towards the front of the package rack;

wherein the counting device is an automated system;

wherein the counting device counts the total number of packs contained within the plurality of prepackaged smoking materials;

wherein the counting device counts the total number of packs contained with each track selected from the plurality of carton trays of the package rack;

wherein the counting device comprises a logic module, a wavefront generator, a wavefront sensor, and a display;

wherein the logic module is further defined with a timing circuit;

wherein the wavefront generator is electrically connected to the logic module;

wherein the wavefront sensor is electrically connected to the logic module;

wherein the display is electrically connected to the logic module;

wherein the counting device further comprises a reflecting surface;

wherein the reflecting surface attaches to the pushing device of the track;

wherein the reflecting surface is a smooth and reflective surface that is mounted on the rear side of the pushing device;

wherein the wavefront generator is an electrical device that generates a wavefront;

wherein the wavefront generator is mounted on the rear side of each track such that the generated wavefront moves towards the pushing device;

wherein the wavefront sensor is an electrical sensor that detects the wavefront;

wherein the wavefront sensor is mounted on the rear side of each track such that the reflected wavefront is detected by the wavefront sensor;

wherein the display is an electrical device that is used to display pack count data as accumulated by the counting device;

wherein the wavefront is a wave based source of energy that travels at a constant speed;

wherein the wavefront generator comprises a speaker;

wherein the wavefront sensor comprises a microphone;

wherein the counting device further comprises a trigger, a first pull down resistor, and an externally provided voltage referred to as the Vcc;

wherein the trigger, the pull down resistor and the Vcc are electrically interconnected;

wherein the trigger is a momentary switch that is used to initiate the counting device;

wherein the first pull down resistor is an electrical resistor that presents the Vcc to the logic module to indicate that the trigger has been actuated;

wherein the trigger is wired in series between the Vcc and the first pull down resistor;

wherein the first pull down resistor is wired in series between the trigger and an electrical ground;

wherein the logic module detects the Vcc across the first pull down resistor between the trigger and the first pull down resistor;

wherein the wavefront generator comprises a LED;

wherein the wavefront sensor comprises a photoswitch;

wherein the counting device further comprises a communication module, a second pull down resistor, a limit resistor, and an externally provided voltage referred to as the Vcc;

wherein the communication module is electrically connected to the logic module;

wherein the photoswitch, the Vcc, the second pull down resistor, and the logic module are electrically interconnected;

wherein limit resistor, the LED, and the logic module are electrically connected;

wherein the logic module is programmable electronic device;

wherein the LED is an electrical device;

wherein the photoswitch is actuated by light;

wherein the photoswitch closes in the presence of light and to opens in the absence of light;

wherein the second pull down resistor is an electrical resistor that is presents the Vcc to the logic module to indicate that the photoswitch has detected the wavefront;

wherein the limit resistor is an electrical resistor;

wherein the limit resistor limits current flow through the LED;

wherein the communication module is a wireless electronic communication device that allows the logic module to communicate with an externally provided electronic device;

wherein the communication module creates a wireless link with the externally provided electronic device;

wherein the photoswitch is wired in series between the Vcc and the second pull down resistor;

wherein the second pull down resistor is wired in series between the photoswitch and an electrical ground;

wherein the logic module detects the Vcc across the second pull down resistor between the photoswitch and the second pull down resistor;

wherein the logic module further transmits the accumulated pack count information over the wireless link to the externally provided electronic device using the communication module;

wherein the communication module communicates SMS and MMS messages between the logic module and the externally provided electronic device of an appropriate authority through a commercially provided and publicly available cellular wireless network;

wherein upon detection of the wavefront, the logic module ends the operation of the timing device and calculates the distance from the wavefront generator to the wavefront sensor using a time and the speed of the wavefront.

\* \* \* \* \*